US00PP27012P2

(12) United States Plant Patent
Hofmann

(10) Patent No.: US PP27,012 P2
(45) Date of Patent: Aug. 2, 2016

(54) ***CLEOME* PLANT NAMED 'INCLENINRO'**

(50) Latin Name: *Cleome hybrida*
Varietal Denomination: Incleninro

(71) Applicant: Silvia Hofmann, Mainz (DE)

(72) Inventor: Silvia Hofmann, Mainz (DE)

(73) Assignee: Innovaplant Zierpflanzen GmbH & Co. KG, Gensingen (DE)

( * ) Notice: Subject to any disclaimer, the term of this patent is extended or adjusted under 35 U.S.C. 154(b) by 102 days.

(21) Appl. No.: 14/121,720

(22) Filed: Oct. 11, 2014

(51) Int. Cl.
*A01H 5/02* (2006.01)

(52) U.S. Cl.
USPC ..... Plt./416

(58) Field of Classification Search
USPC ..... Plt./413
See application file for complete search history.

*Primary Examiner* — Susan McCormick Ewoldt
(74) *Attorney, Agent, or Firm* — C A. Whealy

(57) ABSTRACT

A new and distinct cultivar of *Cleome* plant named 'Incleninro', characterized by its compact, upright and rounded plant habit; freely branching habit; dense and bushy plant form; spineless stems; freely flowering habit; purple violet-colored sterile flowers; and good garden performance.

1 Drawing Sheet

Botanical designation: *Cleome hybrida.*
Cultivar denomination: 'INCLENINRO'.

BACKGROUND OF THE INVENTION

The present invention relates to a new and distinct cultivar of *Cleome* plant, botanically known as *Cleome hybrida* and hereinafter referred to by the name 'Incleninro'.

The new *Cleome* plant is a product of a planned breeding program conducted by the Inventor in Heidesheim, Germany. The objective of the breeding program was to develop new compact *Cleome* plants with spineless stems, large flowers and flower sterility.

The new *Cleome* plant originated from a cross-pollination made by the Inventor in July, 2010, of a proprietary selection of *Cleome hybrida* identified as code number Cl 10 6-1, not patented, as the female, or seed, parent with a proprietary selection of the *Cleome hybrida* identified as code number 10-01, not patented, as the male, or pollen, parent. The new *Cleome* plant was discovered and selected by the Inventor as a flowering plant within the progeny of the stated cross-pollination in a controlled greenhouse environment in Heidesheim, Germany in April, 2011.

Asexual reproduction of the new *Cleome* plant by cuttings in a controlled greenhouse environment in Heidesheim, Germany since June, 2011 has shown that the unique features of this new *Cleome* plant are stable and reproduced true to type in successive generations.

SUMMARY OF THE INVENTION

Plants of the new *Cleome* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Incleninro'.

These characteristics in combination distinguish 'Incleninro' as a new and distinct *Cleome* plant:

1. Compact, upright and rounded plant habit.
2. Freely branching habit; dense and bushy plant form.
3. Spineless stems.
4. Freely flowering habit.
5. Purple violet-colored sterile flowers.
6. Good garden performance.

Plants of the new *Cleome* differ primarily from plants of the female parent selection in the following characteristics:

1. Plants of the new *Cleome* have spineless stems whereas plants of the female parent selection have stems with spines.
2. Plants of the new *Cleome* have sterile flowers whereas plants of the female parent selection have fertile flowers.

Plants of the new *Cleome* differ primarily from plants of the male parent selection in the following characteristics:

1. Plants of the new *Cleome* have spineless stems whereas plants of the male parent selection have stems with spines.
2. Plants of the new *Cleome* have sterile flowers whereas plants of the male parent selection have fertile flowers.
3. Plants of the new *Cleome* and the male parent selection differ in flower color as plants of the male parent selection have white-colored flowers.

Plants of the new *Cleome* can be compared to plants of *Cleome hybrida* 'Inncleosr', disclosed in U.S. Plant Pat. No. 19,733. In side-by-side comparisons conducted in Heidesheim, Germany, plants of the new *Cleome* and 'Inncleosr' differed in the following characteristics:

1. Plants of the new *Cleome* were more compact than plants of 'Inncleosr'.
2. Plants of the new *Cleome* were more freely branching than plants of 'Inncleosr'.
3. Plants of the new *Cleome* were more freely flowering than plants of 'Inncleosr'.

Plants of the new *Cleome* can also be compared to plants of *Cleome hybrida* 'Inclesnabl', disclosed in U.S. Plant patent application Ser. No. 13/573,174 (now abandoned). In side-by-side comparisons conducted in Heidesheim, Germany, plants of the new *Cleome* and 'Inclesnabl' differed in the following characteristics:

1. Plants of the new *Cleome* were more compact than plants of 'Inclesnabl'.
2. Plants of the new *Cleome* were more freely branching than plants of 'Inclesnabl'.
3. Plants of the new *Cleome* and 'Inclesnabl' differed in flower color as plants of 'Inclesnabl' had white-colored flower blushed with light pink towards the apex.

BRIEF DESCRIPTION OF THE PHOTOGRAPHS

The accompanying colored photographs illustrate the overall appearance of the new *Cleome* plant showing the colors as true as it is reasonably possible to obtain in colored reproductions of this type. Colors in the photographs may differ slightly from the color values cited in the detailed botanical description which accurately describe the colors of the new *Cleome* plant.

The photograph at the bottom of the sheet comprises a side perspective view of a typical flowering plant of 'Incleninro' grown in a container.

The photograph at the top of the sheet is a close-up view of a typical flowering plant of 'Incleninro'.

DETAILED BOTANICAL DESCRIPTION

The aforementioned photographs and following observations, measurements and values describe plants grown during the spring in 10-cm containers in an outdoor nursery in Bonsall, Calif. and under commercial practices typical of commercial *Cleome* production. During the production of the plants, day temperatures averaged 24° C., night temperatures ranged from 16° C. to 18° C. and light levels averaged 7,000 foot-candles. Plants were pinched one time and were six weeks old when the photographs and description were taken. Plants were grown under long day/short night conditions to induce flower initiation and development. In the following description, color references are made to The Royal Horticultural Society Colour Chart, 2007 Edition, except where general terms of ordinary dictionary significance are used.

Botanical classification: *Cleome hybrida* 'Incleninro'.

Parentage:

*Female, or seed, parent*.—Proprietary selection of *Cleome hybrida* identified as code number Cl 10 6-1, not patented.

*Male, or pollen parent*.—Proprietary selection of *Cleome hybrida* identified as code number 10-01, not patented.

Propagation:

*Type*.—By vegetative cuttings.

*Time to initiate roots, summer*.—About five to seven days at soil temperatures about 21° C.

*Time to initiate roots, winter*.—About seven to nine days at soil temperatures about 21° C.

*Time to produce a rooted young plant, summer*.—About twelve days at soil temperatures about 21° C.

*Time to produce a rooted young plant, winter*.—About 15 days at soil temperatures about 21° C.

*Root description*.—Medium in thickness, fibrous; white in color.

*Rooting habit*.—Moderately freely branching; medium density.

Plant description:

*Plant and growth habit*.—Herbaceous perennial; compact, upright and rounded plant habit; vigorous growth habit.

*Branching habit*.—Freely branching habit, when pinched, about four primary lateral branches each with two to three secondary lateral branches develop.

*Plant height*.—About 32 cm.

*Plant width (spread)*.—About 28 cm.

*Lateral branches*.—Length: About 32 cm. Diameter: About 7 mm. Internode length: About 2.7 cm. Strength: Strong. Texture: Pubescent, minute; no spines observed. Color: Close to 146B.

Leaf description:

*Arrangement*.—Alternate; palmately compound with five to occasionally seven leaflets per leaf.

*Fragrance*.—None detected.

*Leaf length*.—About 10.5 cm.

*Leaf width*.—About 10.7 cm.

*Center leaflet length*.—About 6.7 cm.

*Center leaflet width*.—About 3 cm.

*Lateral leaflets length*.—About 5.8 cm.

*Lateral leaflets width*.—About 2.4 cm.

*Lower leaflets length*.—About 4.3 cm.

*Lower leaflets width*.—About 1.9 cm.

*Leaflet shape*.—Elliptical.

*Leaflet apex*.—Acute.

*Leaflet base*.—Attenuate.

*Leaflet margin*.—Entire and slightly sinuate.

*Leaflet texture, upper and lower surfaces*.—Scattered pubescence; minute.

*Venation pattern*.—Pinnate, arcuate.

*Color*.—Developing leaflets, upper surface: Close to 146A. Developing leaflets, lower surface: Close to 146B. Fully expanded leaflets, upper surface: Close to 147A; venation, close to 146C. Fully expanded leaflets, lower surface: Close to 146A; venation, close to 146D.

*Leaf petiole length*.—About 8.2 cm.

*Leaf petiole diameter*.—About 3.2 mm.

*Leaf petiole texture, upper and lower surfaces*.—Pubescent, minute.

*Leaf petiole color, upper surface*.—Close to 146C.

*Leaf petiole color, lower surface*.—Close to 146B.

Flower description:

*Flower type and flowering habit*.—Single zygomorphic flowers arranged in short terminal racemes; flowers face upright to outwardly; freely flowering habit with about 48 flowers developing per raceme.

*Fragrance*.—None detected.

*Natural flowering season*.—Long flowering period; plants flower continuously from spring until frost in southern California.

*Postproduction longevity*.—Flowers last about three days on the plant; flowers not persistent.

*Flower buds*.—Height: About 1.5 cm. Diameter: About 4 mm. Shape: Narrowly elongate. Color: Close to N77B.

*Inflorescence height*.—About 8 cm.

*Inflorescence diameter*.—About 8.5 cm.

*Flower diameter*.—About 3 cm.

*Flower height*.—About 2.1 cm.

*Flower depth*.—About 2.1 cm.

*Petals*.—Quantity per flower: Typically four in a single whorl. Length: About 1.7 cm. Width: About 8 mm.

Shape: Elliptical. Apex: Broadly acute. Base: Attenuate. Margin: Entire. Texture, upper and lower surfaces: Smooth, glabrous; velvety. Color: When opening, upper surface: Center, close to N80C; towards the apex, close to N77B; towards the base, close to 157B. When opening, lower surface: Center, close to N77C; towards the apex, close to N79D; towards the base, close to 157B. Fully opened, upper surface: Close to N81C; towards the base, close to N81D; color becoming entirely white, close to N81D, with development. Fully opened, lower surface: Center, close to N81C; towards the apex, close to N81B; towards the base, close to N81D.

*Sepals*.—Quantity per flower: Typically four in a single whorl. Length: About 5 mm. Width: About 2 mm. Shape: Lanceolate. Apex: Acute. Base: Truncate. Margin: Entire. Texture, upper surface: Smooth, glabrous. Texture, lower surface: Pubescent, minute. Color, upper surface: Close to 199A. Color, lower surface: Close to 199C.

*Peduncles*.—Length: About 2.4 cm. Diameter: About 2.5 mm. Angle: Mostly upright. Strength: Strong; flexible. Texture: Pubescent, minute. Color: Close to 146C.

*Pedicels*.—Length: About 2 cm. Diameter: About 1 mm. Angle: About 15° to 75° from peduncle axis. Strength: Strong; flexible. Texture: Pubescent, minute. Color: Close to 152B.

*Flower bracts*.—Quantity and arrangement: One subtending each flower; sessile. Length: About 2 cm. Width: About 1 cm. Shape: Cordate. Texture, upper and lower surfaces: Smooth, glabrous. Color, upper and lower surfaces: Close to 146A.

*Reproductive organs*.—Stamens: Quantity per flower: Typically five. Filament length: About 2 mm. Filament color: Close to 152B. Anther shape: Lanceolate. Anther length: About 5 mm. Anther color: Close to 152D. Pollen amount: None observed; flowers sterile. Pistils: Quantity per flower: One. Pistil length: About 2.5 cm; long and extended. Stigma shape: Rounded. Stigma color: Close to N79B. Style length: About 2.3 cm. Style color: Close to N79A. Ovary color: Close to 152D.

*Fruits and seeds*.—Fruit and seed development have not been observed on plants of the new *Cleome*.

Disease & pest resistance: Plants of the new *Cleome* have not been noted to be resistant to pathogens and pests common to *Cleome* plants.

Garden performance: Plants of the new *Cleome* have been observed to have good garden performance and tolerate rain, wind and temperatures ranging from about 1° C. to 35° C.

It is claimed:

1. A new and distinct *Cleome* plant named 'Incleninro' as illustrated and described.

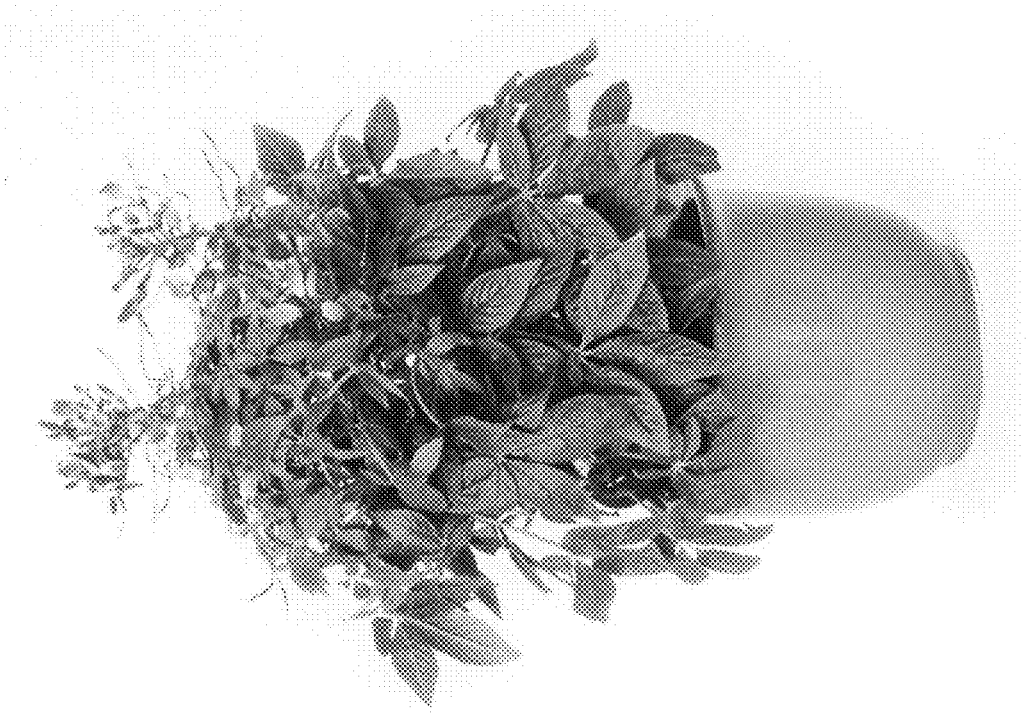
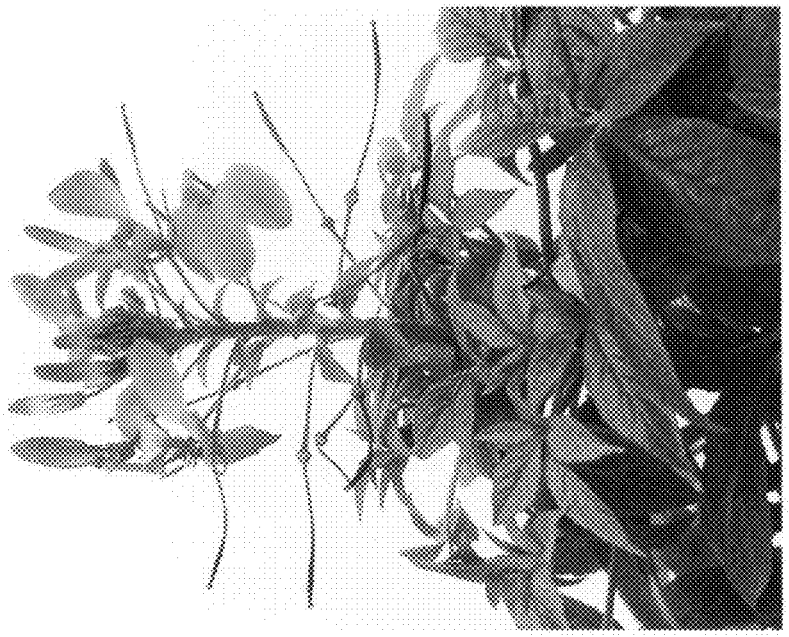

* * * * *